United States Patent
Conlan et al.

(10) Patent No.: US 11,291,759 B2
(45) Date of Patent: Apr. 5, 2022

(54) LIPOSUCTION DEVICE AND USE THEREOF

(71) Applicant: AURASTEM LLC, Solana Beach, CA (US)

(72) Inventors: Bradford A. Conlan, Solana Beach, CA (US); Lucas Fornace, Encinitas, CA (US)

(73) Assignee: AURASTEM LLC, Solana Beach, CA (US)

( * ) Notice: Subject to any disclaimer, the term of this patent is extended or adjusted under 35 U.S.C. 154(b) by 474 days.

(21) Appl. No.: 16/242,888

(22) Filed: Jan. 8, 2019

(65) Prior Publication Data

US 2019/0143005 A1 May 16, 2019

Related U.S. Application Data

(63) Continuation of application No. 15/422,304, filed on Feb. 1, 2017, now Pat. No. 10,183,101, which is a
(Continued)

(51) Int. Cl.
*A61M 1/00* (2006.01)
*A61M 5/31* (2006.01)
(Continued)

(52) U.S. Cl.
CPC ............. *A61M 1/84* (2021.05); *A61M 1/67* (2021.05); *A61M 1/79* (2021.05); *A61M 1/815* (2021.05); *A61M 1/88* (2021.05); *A61M 5/3145* (2013.01); *A61M 37/0015* (2013.01); *A61B 2017/00792* (2013.01); *A61M 5/3291* (2013.01);
(Continued)

(58) Field of Classification Search
CPC .......... A61M 1/67; A61M 1/79; A61M 1/815; A61M 1/84; A61M 1/88; A61M 5/3291; A61M 2202/08; A61M 2202/0007; A61M 2202/0014; A61M 1/81; A61M 1/82;
(Continued)

(56) References Cited

U.S. PATENT DOCUMENTS 3,840,008 A 10/1974 Noiles
4,713,053 A 12/1987 Lee
(Continued)

FOREIGN PATENT DOCUMENTS

AU 2004240645 12/2004
CN 201492455 6/2010
(Continued)

OTHER PUBLICATIONS

Conlan, Bradford; Notice of Rejection for Japanese Application No. 2018-528192, filed Jul. 1, 2016; dated Aug. 4, 2020; 10 pages.
(Continued)

*Primary Examiner* — Susan S Su
(74) *Attorney, Agent, or Firm* — Fish & Richardson P.C.

(57) ABSTRACT

Embodiments of the present invention disclose a method of cosmetic or biomedical application of a device, comprising a self-contained syringe device comprising an inner syringe included within an outer syringe and wherein a filter is attached inside the outer syringe barrel; wherein the filter comprises a filter material that prevents premature filter collapse where the filter material is optionally coated to increase stiffness, and wherein liposuctioned adipose tissue is collected and purified inside the syringes.

15 Claims, 5 Drawing Sheets

Related U.S. Application Data continuation-in-part of application No. 15/199,773, filed on Jun. 30, 2016, now Pat. No. 10,188,777.

(60) Provisional application No. 62/207,746, filed on Aug. 20, 2015.

(51) Int. Cl.
*A61M 37/00* (2006.01)
*A61M 5/32* (2006.01)
*A61B 17/00* (2006.01)

(52) U.S. Cl.
CPC .............. *A61M 2202/0007* (2013.01); *A61M 2202/0014* (2013.01); *A61M 2202/08* (2013.01); *A61M 2205/7563* (2013.01)

(58) Field of Classification Search
CPC ...... A61M 2205/7563; A61M 2205/75; A61M 5/3145; A61B 2017/00792
See application file for complete search history.

(56) References Cited

U.S. PATENT DOCUMENTS

| | | | |
|---|---|---|---|
| 5,002,538 | A | 3/1991 | Johnson |
| 5,744,360 | A | 4/1998 | Hu et al. |
| 5,817,050 | A | 10/1998 | Klein |
| 5,911,700 | A | 6/1999 | Mozsary et al. |
| 5,968,008 | A | 10/1999 | Grams |
| 6,020,196 | A | 2/2000 | Hu et al. |
| 6,261,310 | B1 | 7/2001 | Neuberger et al. |
| 7,390,484 | B2 | 6/2008 | Fraser et al. |
| 7,608,048 | B2 | 10/2009 | Goldenberg |
| 7,651,684 | B2 | 1/2010 | Hedrick et al. |
| 7,841,991 | B2 | 11/2010 | Douglas et al. |
| 7,914,504 | B2 | 3/2011 | Klein |
| 8,202,493 | B2 | 6/2012 | Buss |
| 8,489,172 | B2 | 7/2013 | Gelbart et al. |
| 8,652,123 | B2 | 2/2014 | Gurtner et al. |
| 9,133,431 | B2 | 9/2015 | Peterson et al. |
| 10,183,101 | B2 | 1/2019 | Conlan et al. |
| 10,188,777 | B2 | 1/2019 | Conlan et al. |
| 2002/0151874 | A1 | 10/2002 | Kolster et al. |
| 2002/0169469 | A1 | 11/2002 | Klein |
| 2003/0167053 | A1 | 9/2003 | Taufig |
| 2004/0044331 | A1 | 3/2004 | Klein |
| 2005/0025755 | A1 | 2/2005 | Hedrick et al. |
| 2005/0054947 | A1 | 3/2005 | Goldenberg |
| 2005/0131439 | A1 | 6/2005 | Brett |
| 2006/0079921 | A1 | 4/2006 | Nezhat et al. |
| 2006/0293722 | A1 | 12/2006 | Slatkine et al. |
| 2007/0010810 | A1 | 1/2007 | Kochamba |
| 2007/0055179 | A1 | 3/2007 | Deem et al. |
| 2007/0100277 | A1 | 5/2007 | Shippert |
| 2007/0225686 | A1 | 9/2007 | Shippert |
| 2007/0270710 | A1 | 11/2007 | Frass et al. |
| 2007/0270745 | A1 | 11/2007 | Nezhat et al. |
| 2008/0058851 | A1 | 3/2008 | Edelstein et al. |
| 2008/0154240 | A1 | 6/2008 | Shippert |
| 2008/0275473 | A1 | 11/2008 | Filipi et al. |
| 2009/0088823 | A1 | 4/2009 | Barak et al. |
| 2010/0057056 | A1 | 3/2010 | Gurtner et al. |
| 2010/0125240 | A1 | 5/2010 | Spedden et al. |
| 2010/0137841 | A1 | 6/2010 | Khouri et al. |
| 2010/0228182 | A1 | 9/2010 | Clark, III et al. |
| 2010/0318070 | A1 | 12/2010 | Mitra et al. |
| 2011/0166509 | A1 | 7/2011 | Gross et al. |
| 2012/0027804 | A1 | 2/2012 | Odermatt et al. |
| 2012/0165725 | A1 | 6/2012 | Chomas et al. |
| 2012/0259311 | A1 | 10/2012 | Hirshberg |
| 2014/0155869 | A1 | 6/2014 | Seare |
| 2014/0257272 | A1 | 9/2014 | Clark, III et al. |
| 2015/0289858 | A1 | 10/2015 | McGillicuddy et al. |
| 2015/0352266 | A1 | 12/2015 | Gourlay |
| 2015/0374888 | A1 | 12/2015 | Shippert |
| 2016/0058924 | A1 | 3/2016 | Kim |
| 2016/0106889 | A1 | 4/2016 | Conlan et al. |
| 2017/0021066 | A1 | 1/2017 | Sforza |
| 2017/0049942 | A1 | 2/2017 | Conlan |
| 2017/0049972 | A1 | 2/2017 | Persons |
| 2017/0203040 | A1 | 7/2017 | Conlan |
| 2017/0303956 | A1 | 10/2017 | Misle et al. |
| 2017/0368226 | A1 | 12/2017 | Pilkington et al. |
| 2018/0117263 | A1 | 5/2018 | Cumbo |
| 2018/0207331 | A1 | 7/2018 | Conlan et al. |
| 2019/0046231 | A1 | 2/2019 | Conlan et al. |
| 2019/0143005 | A1 | 5/2019 | Conlan et al. |

FOREIGN PATENT DOCUMENTS

| | | |
|---|---|---|
| CN | 202400999 | 8/2012 |
| CN | 202982795 | 6/2013 |
| EP | 0331313 | 9/1989 |
| EP | 2404547 | 1/2012 |
| GB | 2402345 | 10/2005 |
| JP | H1050551 | 6/1998 |
| JP | 2005523082 | 8/2005 |
| JP | 2010246939 | 11/2010 |
| JP | 2016525897 | 9/2016 |
| WO | 9601085 | 1/1996 |
| WO | 2008028126 | 3/2008 |
| WO | 2012154284 | 11/2012 |
| WO | 20120154284 | 11/2012 |
| WO | 2017030665 | 2/2017 |
| WO | 2018200002 | 11/2018 |

OTHER PUBLICATIONS

Conlan, Bradford, Extended European Search Report for EP Application No. 16837442.9, filed Jul. 1, 2016; dated Jul. 3, 2019, 11 pages.

Conlan, Bradford A.; Partial Supplementary European Search Report for serial No. 16837442.9, filed Jul. 1, 2016, dated Mar. 14, 2019, 12 pgs.

Guan, Zhaohui; First Office Action for Chinese Application No. 201680057204.6 filed Jul. 1, 2016; dated Jan. 21, 2020; 8 pages of English translation.

Fornace, Lucas; International Preliminary Report of Patentability for PCT Application No. PCT/US2017/030247, filed Apr. 28, 2017, dated Nov. 7, 2019, 7 pages.

Bradford, Conlan; Extended European Search Report for Application No. 17907962.9, filed Nov. 25, 2019, dated Nov. 12, 2020, 8 pages.

Conlan, Bradford A.; Non-Final Office Action for U.S. Appl. No. 16/164,183, filed Oct. 18, 2018, dated Apr. 22, 2021, 54 pgs.

Conlan, Bradford A.; Chinese Office Action for Application No. 2020-509418, filed Apr. 28, 2017, dated Feb. 9, 2021, 9 pgs.

Conlan, Bradford A.; Issue Notification for U.S. Appl. No. 15/199,773, filed Jun. 30, 2016, dated Jan. 9, 2019, 1 pg.

Conlan, Bradford A.; Non-Final Office Action for U.S. Appl. No. 15/199,773, filed Jun. 30, 2016, dated Sep. 27, 2018, 22 pgs.

Conlan, Bradford; Notice of Allowance for U.S. Appl. No. 15/199,773, filed Jun. 30, 2016, dated Nov. 26, 2018, 11 pgs.

Conlan, Bradford A.; Issue Notification for U.S. Appl. No. 15/422,304, filed Feb. 1, 2017, dated Jan. 1, 2019, 1 pg.

Conlan, Bradford A.; Non-Final Office Action for U.S. Appl. No. 15/422,304, filed Feb. 1, 2017, dated Sep. 27, 2018, 16 pgs.

Conlan, Bradford; Corrected Notice of Allowance for U.S. Appl. No. 15/422,304, filed Feb. 1, 2017, dated Dec. 20, 2018, 3 pgs.

Conlan, Bradford; Notice of Allowance for U.S. Appl. No. 15/422,304, filed Feb. 1, 2017, dated Nov. 26, 2018, 12 pgs.

Colan, Bradford A.; International Search Report and Written Opinion for PCT/US17/30247, filed Apr. 28, 2017, dated Jul. 19, 2017, 8 pgs.

Conlan, Bradford A.; International Preliminary Report on Patentability for PCT/US2016/040761, filed Jul. 1, 2016, dated Feb. 20, 2018, 9 pgs.

Conlan, Bradford A.; International Search Report and Written Opinion for PCT/US2016/040761, filed Jul. 1, 2016, dated Sep. 12, 2016, 14 pgs.

(56) References Cited

OTHER PUBLICATIONS

Conlan, Bradford; Notice of Rejection for Japanese Application No. 2018-528192, filed Jul. 1, 2016; dated May 11, 2021; 4 pages.

LIPOSUCTION DEVICE AND USE THEREOF

CROSS-REFERENCE TO RELATED APPLICATION

This application is a Continuation of U.S. patent application Ser. No. 15/422,304 filed on Feb. 1, 2017. The teaching of this prior application is incorporated herein by reference in its entirety.

FIELD OF THE INVENTION

The invention relates generally to biomedical sciences and technologies and particularly to tissue harvesting and tissue graft application devices and methods.

BACKGROUND OF THE INVENTION

The transfer of adipose tissue to various regions of the body is a relatively common cosmetic, therapeutic and structural procedure involving the harvest of adipose tissue from one location and re-implantation of the harvested and, oftentimes processed tissue, in another location (see Coleman 1995; and Coleman 2001). While being largely used for repair of small cosmetic defects such as facial folds, wrinkles, pock marks and divots; the transfer of adipose tissue has recently been used for cosmetic and/or therapeutic breast augmentation and reconstruction (Bircoll and Novack 1987; and Dixon 1988), and augmentation of the buttocks (Cardenas-Camarena, Lacouture et al. 1999; de Pedroza 2000; and Peren, Gomez et al. 2000).

In the past, adipose tissue grafts and methods of adipose tissue transfer have been plagued with difficulties and side effects including necrosis, absorption of the implant by the body, infection (Castello, Barros et al. 1999; Valdatta, Thione et al. 2001), calcifications and scarring (Huch, Kunzi et al. 1998), inconsistent engraftment, (Eremia and Newman 2000), lack of durability, and other problems arising from lack of neovascularization and necrosis of the transplanted tissue. One of the biggest challenges in adipose tissue transfer is absorption of the implant by the body and volume retention of adipose tissue grafts following transfer. When adipose tissue is harvested or washed, the space between individual pieces of harvested adipose tissue is filled by liquid (e.g., water, blood, tumescent solution, oil). When this tissue/fluid mixture is implanted into a recipient the liquid portion is rapidly absorbed by the body resulting in loss of volume. The process by which the amount of fluid is removed from the tissue/fluid mixture is frequently referred to as "drying the adipose tissue" or "dehydrating the adipose tissue". The content of red and white blood cells and the like within an adipose tissue graft can also significantly affect the volume of graft retained after graft transplantation, due to induction or exacerbation of an inflammatory response. Another aspect of tissue retention relates to the amount of lipid within the adipose tissue graft. It understood that the presence of free lipid (meaning lipids released from dead or damaged adipocytes; also referred to as oil) in adipose tissue grafts can result in induction or exacerbation of an inflammatory response with substantial phagocytic activity and consequent loss of graft volume.

It is also known that mixing unprocessed adipose tissue with a concentrated population of adipose-derived regenerative cells overcomes many of the problems associated with adipose tissue grafts and adipose tissue transfer, as described above. Specifically, supplementing unprocessed adipose tissue with concentrated populations of adipose-derived cells comprising adipose-derived stem cells increases the weight, vascularization, and retention of fat grafts. (See U.S. Pat. No. 7,390,484 and co-pending U.S. Patent Application Publication No. 2005/0025755, issued on Jan. 26, 2010 as U.S. Pat. No. 7,651,684, herein expressly incorporated by reference in their entireties). Adipose tissue fragments supplemented, or mixed, with a concentrated population of cells including adipose-derived stem cells exhibit improved neoangiogeneis and perfusion in grafts when compared to unsupplemented grafts of adipose tissue alone in animal models. Further, adipose tissue grafts supplemented with adipose-derived regenerative cells that comprise adipose derived stem cells show increased graft retention and weight over time, when compared to unsupplemented grafts. (See U.S. Patent Application Publication No. 2005/0025755, issued on Jan. 26, 2010 as U.S. Pat. No. 7,651,684). Further, the processing of adipose tissue in a closed, sterile fluid pathway greatly reduces the chance of infection. The improvement in autologous transfer of adipose tissue seen in the animal models described above has also been replicated in human clinical studies. Nevertheless, the isolation and purification of concentrated populations of adipose-derived regenerative cells comprising adipose-derived stem cells (ADSCs), usually involves a series of washing, digestion, filtration and/or centrifugation steps, which can reduce the yield of viable cells, require mechanical equipment and specialized clinicians, and/or can compromise the quality, appearance, longevity, hydration or efficacy of the graft.

Additionally, stresses could cause undesirable reactions to harvested adipose tissues. Such stresses include, for example, exposure to environmental pathogens, which are mentioned above, and prolonged post-harvest storage, etc. Therefore, there is a need for in-situ harvest, cleaning, and use of an adipose tissue graft for biomedical applications.

The need for additional approaches to prepare and optimize adipose tissue grafts and implants and to isolate and/or concentrate adipose-derived regenerative cells is manifest.

SUMMARY OF THE INVENTION

In one aspect of the present invention, it is provided an adipose tissue collection and purification device comprising a self-contained syringe device comprising an inner syringe included within an outer syringe, wherein a filter or a series of filters (e.g., a 2 stage or 3 stage filter) is attached inside the outer syringe barrel, wherein a filter or a series of filters (e.g., a 2 stage or 3 stage filter) is attached inside the outer syringe barrel, wherein the filter comprises a filter material, and wherein lipoaspirated adipose tissue is collected and purified inside the syringes.

In some embodiments of the invention device, optionally in one or more invention embodiments disclosed herein, the filter comprises a filter material that is coated so as to increase stiffness and prevent premature filter collapse.

In some embodiments of the invention device, optionally in one or more invention embodiments disclosed herein, the filter has a mesh pore size between 30 micro meters and 3000 micro meters, e.g., 1200 micro meters or 2500 micro meters.

In some embodiments of the invention device, optionally in one or more invention embodiments disclosed herein, the inner syringe contained within the outer syringe is able to evacuate the waste product from lipoaspirated tissue into its barrel and remain contained within its barrel during the reinjection of remaining adipose contained within the filter of the outer syringe.

In some embodiments of the invention device, optionally in one or more invention embodiments disclosed herein, the inner syringe plunger contains a one-way valve that allows for the passage of lipoaspirate waste into its barrel but does not allow the lipoaspirate waste to re-enter the barrel of the outer syringe.

In some embodiments of the invention device, optionally in one or more invention embodiments disclosed herein, the outer syringe is non-round shaped with a corresponding non-round shaped piston such that the piston is prevented from rotation while the inner syringe is being unscrewed.

In some embodiments of the invention device, optionally in one or more invention embodiments disclosed herein, the inner syringe is an inner waste chamber syringe that allows a waste product to evacuate from the lipoaspirated tissue into a separate waste product chamber.

In some embodiments of the invention device, optionally in one or more invention embodiments disclosed herein, the inner syringe is a syringe of a wash fluid for washing the tissue, while back flowing the filter to clean the filter.

In some embodiments of the invention device, optionally in one or more invention embodiments disclosed herein, the inner syringe is an inner waste chamber syringe that attaches to a piston with a luer-activated port, thus self-sealing when the waste syringe is removed so as to prevent leaking and keep the device a closed system.

In some embodiments of the invention device, optionally in one or more invention embodiments disclosed herein, the outer syringe is added grip so as to overcome an issue of grip caused by slipperiness of the adipose tissue.

In some embodiments of the invention device, optionally in one or more invention embodiments disclosed herein, the non-round shaped syringe provides extra grip to overcome an issue of grip caused by slipperiness of the adipose tissue.

In some embodiments of the invention device, optionally in one or more invention embodiments disclosed herein, the syringe comprises a custom locking mechanism to allow locking in the open position, thereby allowing for holding of a vacuum.

In some embodiments of the invention device, optionally in one or more invention embodiments disclosed herein, the syringe comprises a syringe tip clogging guard added to the end of the syringe.

In some embodiments of the invention device, optionally in one or more invention embodiments disclosed herein, the device further comprises a needle or a needle hub, wherein the needle or needle hub is attached to the self-contained syringe device.

In some embodiments of the invention device, optionally in one or more invention embodiments disclosed herein, the device further comprises a guide that prevents the over insertion and under insertion and thus allows collection of subcutaneous adipose tissue at desired depth.

In some embodiments of the invention device, optionally in one or more invention embodiments disclosed herein, the guide is curved to allow puncture of the needle and forces the needle to remain in the subcutaneous layer of adipose tissue.

In some embodiments of the invention device, optionally in one or more invention embodiments disclosed herein, the guide further contains a mechanism that pinches the exterior of the skin and thus raises the subcutaneous fat layer to allow for insertion of the needle.

In some embodiments of the invention device, optionally in one or more invention embodiments disclosed herein, the guide further contains a mechanism utilizing vacuum to raise the fat layer.

In another aspect of the present invention, it is provided a method, which method comprising collecting and purifying an adipose tissue using a device, wherein the device comprising a self-contained syringe device comprising an inner syringe included within an outer syringe, wherein a filter or a series of filters (e.g., a 2 stage or 3 stage filter) is attached inside the outer syringe barrel, wherein the filter comprises a filter material, and wherein lipoaspirated adipose tissue is collected and purified inside the syringes.

In some embodiments of the invention device, optionally in one or more invention embodiments disclosed herein, the filter comprises a filter material that is coated so as to increase stiffness and prevent premature filter collapse.

In some embodiments of the invention method, optionally in one or more invention embodiments disclosed herein, the filter has a mesh pore size between 30 micrometers and 3000 micrometers, e.g., 1200 micrometers or 2500 micrometers.

In some embodiments of the invention method, optionally in one or more invention embodiments disclosed herein, the inner syringe contained within the outer syringe is able to evacuate the waste product from lipoaspirated tissue into its barrel and remains contained within its barrel during the reinjection of remaining adipose contained within the filter of the outer syringe.

In some embodiments of the invention method, optionally in one or more invention embodiments disclosed herein, the inner syringe plunger contains a one-way valve that allows for the passage of lipoaspirate waste into its barrel but does not allow the lipoaspirate waste to re-enter the barrel of the outer syringe.

In some embodiments of the invention method, optionally in one or more invention embodiments disclosed herein, the outer syringe is non-round shaped with a corresponding non-round shaped piston such that the piston is prevented from rotation while the inner syringe is being unscrewed.

In some embodiments of the invention method, optionally in one or more invention embodiments disclosed herein, the inner syringe is an inner waste chamber syringe that allows a waste product to evacuate from the lipoaspirated tissue into a separate waste product chamber.

In some embodiments of the invention method, optionally in one or more invention embodiments disclosed herein, the inner syringe is a syringe of a wash fluid for washing the tissue, while back flowing the filter to clean the filter.

In some embodiments of the invention method, optionally in one or more invention embodiments disclosed herein, the inner syringe is an inner waste chamber syringe that attaches to a piston with a luer-activated port, thus self-sealing when the waste syringe is removed so as to prevent leaking and keep the device a closed system.

In some embodiments of the invention method, optionally in one or more invention embodiments disclosed herein, the outer syringe is added grip so as to overcome an issue of grip caused by slipperiness of the adipose tissue.

In some embodiments of the invention method, optionally in one or more invention embodiments disclosed herein, the non-round shaped syringe provides extra grip to overcome an issue of grip caused by slipperiness of the adipose tissue.

In some embodiments of the invention method, optionally in one or more invention embodiments disclosed herein, the syringe comprises a custom locking mechanism to allow locking in the open position, thereby allowing for holding of a vacuum.

In some embodiments of the invention method, optionally in one or more invention embodiments disclosed herein, the syringe comprises a syringe tip clogging guard added to the end of the syringe.

In some embodiments of the invention method, optionally in one or more invention embodiments disclosed herein, the device further comprises a needle or a needle hub, wherein the needle or needle hub is attached to the self-contained syringe device.

In some embodiments of the invention method, optionally in one or more invention embodiments disclosed herein, the device further comprises a guide that prevents the over insertion and under insertion and thus allows collection of subcutaneous adipose tissue at desired depth.

In some embodiments of the invention method, optionally in one or more invention embodiments disclosed herein, the guide is curved to allow puncture of the needle and forces the needle to remain in the subcutaneous layer of adipose tissue.

In some embodiments of the invention method, optionally in one or more invention embodiments disclosed herein, the guide further contains a mechanism that pinches the exterior of the skin and thus raises the subcutaneous fat layer to allow for insertion of the needle.

In some embodiments of the invention method, optionally in one or more invention embodiments disclosed herein, the guide further contains a mechanism utilizing vacuum to raise the fat layer.

In some embodiments of the invention method, optionally in combination with any or all the various embodiments described herein, the subject is a human being.

DETAILED DESCRIPTION OF EMBODIMENTS OF THE INVENTION

Definitions

Figure 1:
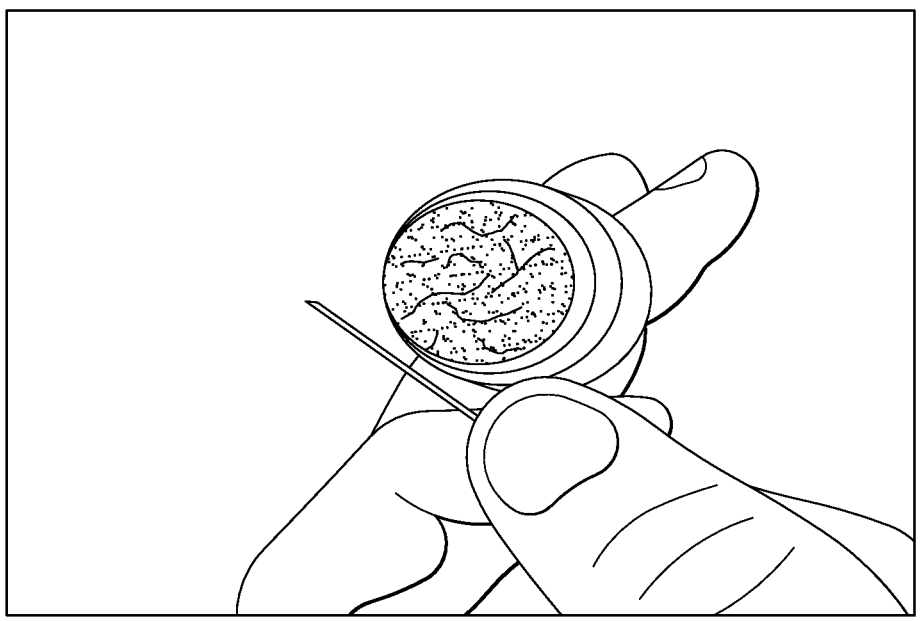
FIG. 1 and FIG. 2 show various elements that can be used to form an embodiment device of the present invention.

As used herein, the term "adipose tissue" is used interchangeably with the term "fat", the meaning of which is well known to a person of ordinary skill in the art.

As used herein, the term "adipose tissue removal" or "tissue removal" or "harvesting" or "liposuction" are used interchangeably to mean remove an amount of adipose tissue from a live subject such as a male or female patient.

As used herein, the term "collapsible" refers to the attribute of a material capable of collapsing under pressure or vacuum or capable of changing of shape or contour or of deformation in response to pressure change, and as such, in some embodiments, the term "collapsible" can mean deformable. An example of a material that is collapsible is a plastic or polymeric material forming a bag, e.g., a bag that is described in U.S. patent application Ser. No. 12/771,985, issued on Sep. 15, 2015 as U.S. Pat. No. 9,133,431, the teachings of which is incorporated herein by reference in its entirety.

As used herein, the term "filter" refers to a porous material having a size or size distribution useful for adipose tissue filtration. Some examples of filter useful for the present invention are described in U.S. patent application Ser. No. 12/771,985, issued on Sep. 15, 2015 as U.S. Pat. No. 9,133,431, the teachings of which is incorporated herein by reference in its entirety.

As used herein, the term "lipoaspirated" and "liposuctioned" can be used interchangeably.

Micro Needles

In some embodiments of the present invention, the invention device can attach to a needle or needles. In some embodiments, the needle can comprise a needle hub that comprises at least one needle that contains between 1-1000 holes around the diameter of the needle barrel which allows passage of adipose tissue and other lipoaspirate.

In some embodiments of the invention device, optionally in combination with any or all the various embodiments disclosed herein, the needle hub comprises a plurality of needles each of which contains between 1-1000 holes around the diameter of the needle barrel which allows passage of adipose tissue and other lipoaspirate.

In some embodiments of the invention device, optionally in combination with any or all the various embodiments disclosed herein, the needle barrel is between 10 and 32 gauge (e.g., 12 or 13 gauge) in diameter.

In some embodiments of the invention device, optionally in combination with any or all the various embodiments disclosed herein, the needle barrel is between 1 mm and 200 mm in length.

In some embodiments of the invention device, optionally in combination with any or all the various embodiments disclosed herein, the holes contained around the diameter of the needle barrel have a geometry that allows for the cutting and removal of lipoaspirate as the device is pushed forward and backwards within the subcutaneous space. In some embodiments, the holes contained around the diameter of the needle barrel have a geometry that allows for the cutting and removal of lipoaspirate as the device is orated within the subcutaneous space.

In some embodiments of the invention device, optionally in combination with any or all the various embodiments disclosed herein, the device further comprising a guide that prevents the over insertion and under insertion and thus allows collection of subcutaneous adipose tissue at desired depth.

In some embodiments of the invention device, optionally in combination with any or all the various embodiments disclosed herein, the guide is curved to allow puncture of the needle and forces the needle to remain in the subcutaneous layer of adipose tissue.

In some embodiments of the invention device, optionally in combination with any or all the various embodiments disclosed herein, the guide further contains a mechanism that pinches the exterior of the skin and thus raises the subcutaneous fat layer to allow for insertion of the needle. In some embodiments, the guide further contains a mechanism utilizing vacuum to raise the fat layer.

Adipose Tissue Collection and Purification

In one aspect of the present invention, it is provided an adipose tissue collection and purification device comprising a self-contained syringe device comprising an inner syringe included within an outer syringe, wherein a filter or a series of filters (e.g., a 2 stage or 3 stage filter) is attached inside the outer syringe barrel, wherein the filter comprises a filter material, and wherein lipoaspirated adipose tissue is collected and purified inside the syringes.

In some embodiments of the invention device, optionally in one or more invention embodiments disclosed herein, the filter comprises a filter material that is coated so as to increase stiffness and prevent premature filter collapse.

In some embodiments of the invention device, optionally in one or more invention embodiments disclosed herein, the filter has a mesh pore size between 30 micro meters and 3000 micro meters, e.g., 1200 micro meters or 2500 micro meters.

In some embodiments of the invention device, optionally in one or more invention embodiments disclosed herein, the inner syringe contained within the outer syringe is able to evacuate the waste product from lipoaspirated tissue into its barrel and remain contained within its barrel during the reinjection of remaining adipose contained within the filter of the outer syringe.

In some embodiments of the invention device, optionally in one or more invention embodiments disclosed herein, the inner syringe plunger contains a one-way valve that allows for the passage of lipoaspirate waste into its barrel but does not allow the lipoaspirate waste to re-enter the barrel of the outer syringe.

In some embodiments of the invention device, optionally in one or more invention embodiments disclosed herein, the outer syringe is non-round shaped with a corresponding non-round shaped piston such that the piston is prevented from rotation while the inner syringe is being unscrewed.

In some embodiments of the invention device, optionally in one or more invention embodiments disclosed herein, the inner syringe is an inner waste chamber syringe that allows a waste product to evacuate from the lipoaspirated tissue into a separate waste product chamber.

In some embodiments of the invention device, optionally in one or more invention embodiments disclosed herein, the inner syringe is a syringe of a wash fluid for washing the tissue, while back flowing the filter to clean the filter.

In some embodiments of the invention device, optionally in one or more invention embodiments disclosed herein, the inner syringe is an inner waste chamber syringe that attaches to a piston with a luer-activated port, thus self-sealing when the waste syringe is removed so as to prevent leaking and keep the device a closed system.

In some embodiments of the invention device, optionally in one or more invention embodiments disclosed herein, the outer syringe is added grip so as to overcome an issue of grip caused by slipperiness of the adipose tissue.

In some embodiments of the invention device, optionally in one or more invention embodiments disclosed herein, the non-round shaped syringe provides extra grip to overcome an issue of grip caused by slipperiness of the adipose tissue.

In some embodiments of the invention device, optionally in one or more invention embodiments disclosed herein, the syringe comprises a custom locking mechanism to allow locking in the open position, thereby allowing for holding of a vacuum.

In some embodiments of the invention device, optionally in one or more invention embodiments disclosed herein, the syringe comprises a syringe tip clogging guard added to the end of the syringe.

In some embodiments of the invention device, optionally in one or more invention embodiments disclosed herein, the device further comprises a needle or a needle hub, wherein the needle or needle hub is attached to the self-contained syringe device.

In some embodiments of the invention device, optionally in one or more invention embodiments disclosed herein, the device further comprises a guide that prevents the over insertion and under insertion and thus allows collection of subcutaneous adipose tissue at desired depth.

In some embodiments of the invention device, optionally in one or more invention embodiments disclosed herein, the guide is curved to allow puncture of the needle and forces the needle to remain in the subcutaneous layer of adipose tissue.

In some embodiments of the invention device, optionally in one or more invention embodiments disclosed herein, the guide further contains a mechanism that pinches the exterior of the skin and thus raises the subcutaneous fat layer to allow for insertion of the needle.

In some embodiments of the invention device, optionally in one or more invention embodiments disclosed herein, the guide further contains a mechanism utilizing vacuum to raise the fat layer.

Figure 3A:
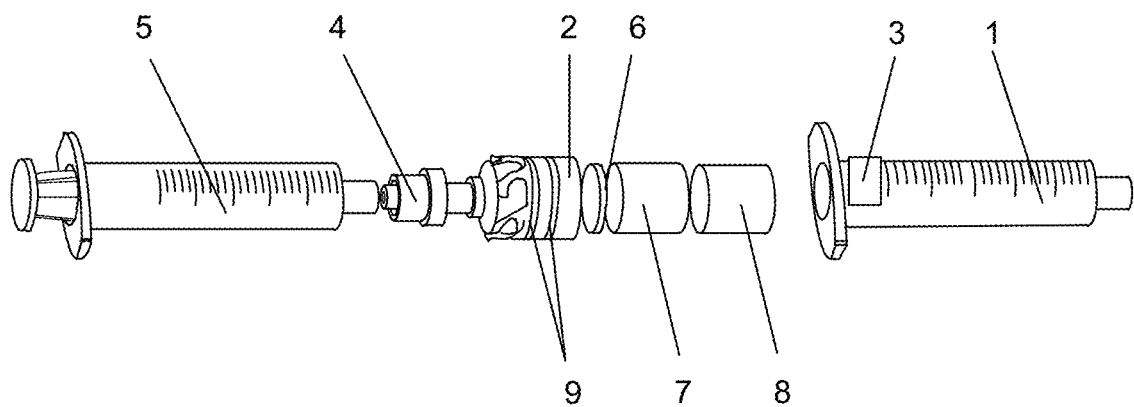
FIG. 3A and FIG. 3B show an embodiment of an invention device.
Figure 3B:
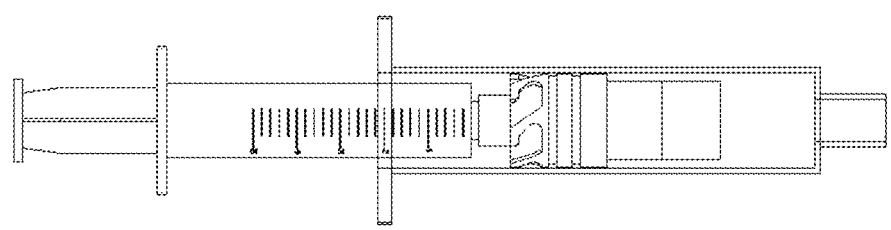

An embodiment of the invention device is described in FIGS. 3A and 3B (PUREGRAFT 10 SYRINGE ASSEMBLY). Referring to FIG. 3A, element 1 is an outer syringe barrel, 2 is a piston, 3 is a locking pin, 4 is a valve (e.g., a check valve), 5 is an inner syringe, which is also referred as a female syringe, 6 is a filter component, which can be, for example, a polyester mesh (e.g., 73 micron with 40% open area), 7 is an additional filter component, which can be, for example, 20 PPI polyester foam, 8 is a further additional filter component, which can be, for example, 45 PPI polyester foam, 6-8 comprising a multiple stage depth filter element of the invention device, and 9 is an O-ring, which can have a size of [2 mm×11 mm ID], made of silicone, e.g. FIG. 3B shows the assembly of the invention device of FIG. 3A.

Figure 4:
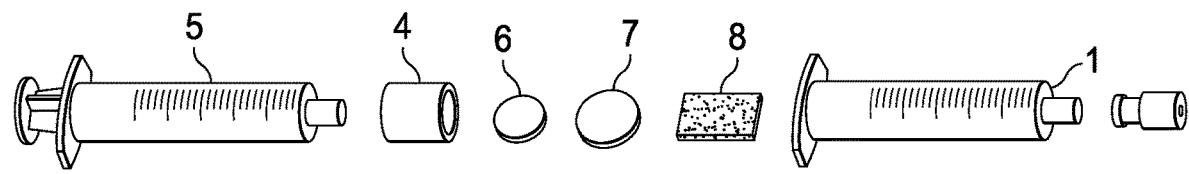
FIG. 4 shows an embodiment of an invention device having an outer syringe and an inner syringe.

Another embodiment of the invention device is described in FIG. 4. Referring to FIG. 4, the invention device embodiment includes 1, an outer syringe barrel, 4, a valve, 5, an inner syringe, 6, a filter component (a mesh), 7, an additional filter component (a foam), and a further additional filter component, 8 (a 73 micron filter disk). In one embodiment, the specifications of the elements of the device in FIG. 4 are the same as the corresponding elements of the device of FIG. 3A.

Figure 6:
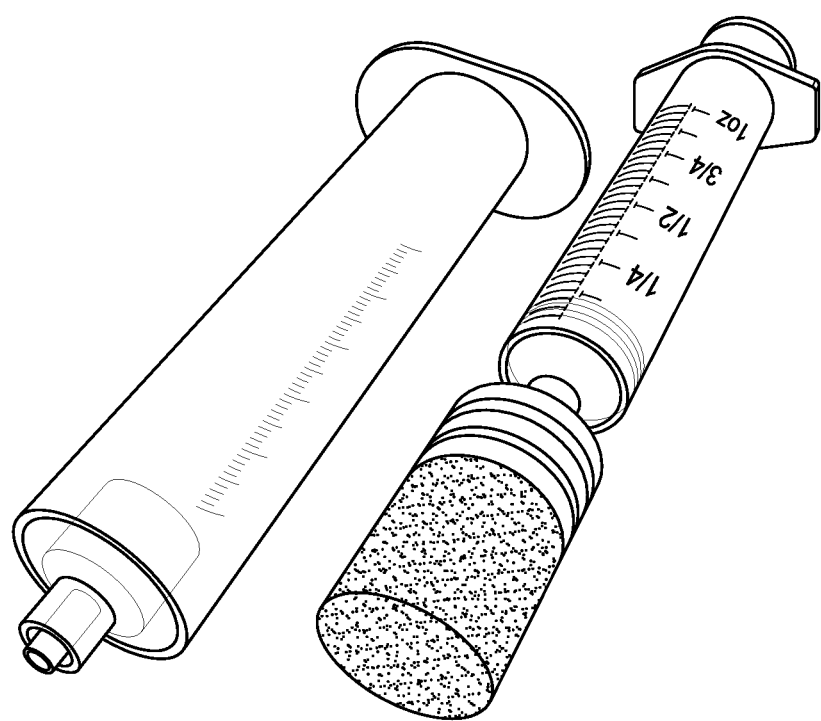
FIG. 6 shows an invention embodiment where a clogging guard (white cylinder) installed on syringe body at left; annular filter design (grey foam material) installed on syringe piston assembly at right.
Figure 7:
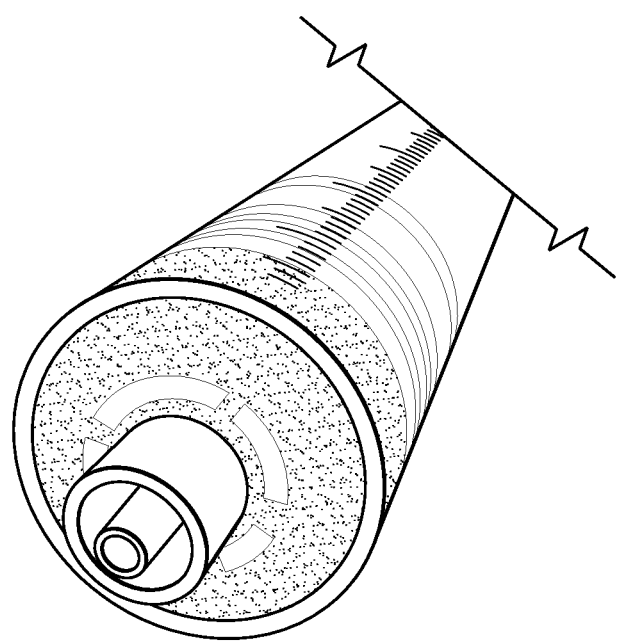
FIG. 7 is a close-up of interaction between clogging guard and annular filter.

FIG. 6-FIG. 9 describe a few further embodiments of the invention syringes. Referring to FIG. 6, a filter is designed to have a geometry of a "annular" design, which provides the maximum surface area (see element 6a in FIG. 6). The filter comprises a filter material that is coated to increase stiffness and prevent premature filter collapse, such a filter is stiff enough to not deform from the filtration pressure, but soft enough to allow one to compress and squeeze out all or substantially all the tissue at the end of the process of invention. In some embodiments, the filter has a mesh pore size between 30 micro meters and 3000 micro meters, e.g., 1200 micro meters or 2500 micro meters.

In some embodiments, the shape of the syringe can be non-round (i.e. square). An advantage of a syringe of a non-round shape is that it prevents piston rotation while a user unscrews the inner waste chamber syringe (see FIG. 9).

Figure 8:
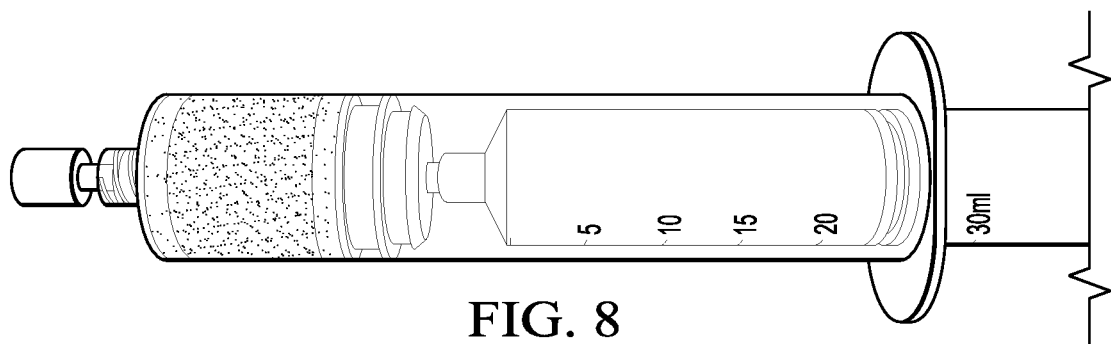
FIG. 8 shows a 60 cc syringe system of invention being used effectively in-lab. The clean tissue is at left; the waste fluid is in the waste syringe at right. The luer-activated valve can be seen center.

In some embodiments, the inner waste chamber of the invention syringe can be replaced with a syringe of wash fluid for washing the tissue, while back flowing the filter to clean the filter. In some embodiments, the waste chamber attaches to the piston with a luer-activated port (element 15 in FIG. 8), thus self-sealing when the waste syringe is removed—without this feature, the syringe would leak and not be a closed system (FIG. 8). Because of the custom shape of the syringe, grip can be added which could be absent on a normal syringe so as to overcome the grip issue caused by slipperiness of the fat tissue.

In some embodiments, the syringe can have a custom locking feature that allows locking in the open position, thus allowing for the holding of vacuum. This design will be unique and easy to use (see FIG. 8).

In some embodiments, a syringe of invention can have a syringe tip clogging guard. Testing by inventors of the present invention revealed a tendency for the final washed fat tissue to clog at the tip of a syringe when being expelled in that the foam filter would clog the port when in contact (data not shown). To address this issue, a "clog guard" can be added to the end of the syringe, which keeps the foam contained and adds numerous fluid paths for the tissue to escape and be expelled (see element 14 in FIG. 6).

Adipose Tissue Harvesting, Collection and Purification Method

In another aspect of the present invention, it is provided a method, which method comprising collecting and purifying an adipose tissue using a device, wherein the device comprising a self-contained syringe device comprising an inner syringe included within an outer syringe, wherein a filter or a series of filters (e.g., a 2 stage or 3 stage filter) is attached inside the outer syringe barrel, wherein the filter comprises a filter material, and wherein lipoaspirated adipose tissue is collected and purified inside the syringes.

In some embodiments of the invention device, optionally in one or more invention embodiments disclosed herein, the filter comprises a filter material that is coated so as to increase stiffness and prevent premature filter collapse.

In some embodiments of the invention method, optionally in one or more invention embodiments disclosed herein, the filter has a mesh pore size between 30 micro meters and 3000 micro meters, e.g., 1200 micro meters or 2500 micro meters.

In some embodiments of the invention method, optionally in one or more invention embodiments disclosed herein, the inner syringe contained within the outer syringe is able to evacuate the waste product from lipoaspirated tissue into its barrel and remain contained within its barrel during the reinjection of remaining adipose contained within the filter of the outer syringe.

In some embodiments of the invention method, optionally in one or more invention embodiments disclosed herein, the inner syringe plunger contains a one-way valve that allows for the passage of lipoaspirate waste into its barrel but does not allow the lipoaspirate waste to re-enter the barrel of the outer syringe.

In some embodiments of the invention method, optionally in one or more invention embodiments disclosed herein, the outer syringe is non-round shaped with a corresponding non-round shaped piston such that the piston is prevented from rotation while the inner syringe is being unscrewed.

In some embodiments of the invention method, optionally in one or more invention embodiments disclosed herein, the inner syringe is an inner waste chamber syringe that allows a waste product to evacuate from the lipoaspirated tissue into a separate waste product chamber.

In some embodiments of the invention method, optionally in one or more invention embodiments disclosed herein, the inner syringe is a syringe of a wash fluid for washing the tissue, while back flowing the filter to clean the filter.

In some embodiments of the invention method, optionally in one or more invention embodiments disclosed herein, the inner syringe is an inner waste chamber syringe that attaches to a piston with a luer-activated port, thus self-sealing when the waste syringe is removed so as to prevent leaking and keep the device a closed system.

In some embodiments of the invention method, optionally in one or more invention embodiments disclosed herein, the outer syringe is added grip so as to overcome an issue of grip caused by slipperiness of the adipose tissue.

In some embodiments of the invention method, optionally in one or more invention embodiments disclosed herein, the non-round shaped syringe provides extra grip to overcome an issue of grip caused by slipperiness of the adipose tissue.

In some embodiments of the invention method, optionally in one or more invention embodiments disclosed herein, the syringe comprises a custom locking mechanism to allow locking in the open position, thereby allowing for holding of a vacuum.

In some embodiments of the invention method, optionally in one or more invention embodiments disclosed herein, the syringe comprises a syringe tip clogging guard added to the end of the syringe.

In some embodiments of the invention method, optionally in one or more invention embodiments disclosed herein, the device further comprises a needle or a needle hub, wherein the needle or needle hub is attached to the self-contained syringe device.

In some embodiments of the invention method, optionally in one or more invention embodiments disclosed herein, the device further comprises a guide that prevents the over insertion and under insertion and thus allows collection of subcutaneous adipose tissue at desired depth.

In some embodiments of the invention method, optionally in one or more invention embodiments disclosed herein, the guide is curved to allow puncture of the needle and forces the needle to remain in the subcutaneous layer of adipose tissue.

In some embodiments of the invention method, optionally in one or more invention embodiments disclosed herein, the guide further contains a mechanism that pinches the exterior of the skin and thus raises the subcutaneous fat layer to allow for insertion of the needle.

In some embodiments of the invention method, optionally in one or more invention embodiments disclosed herein, the guide further contains a mechanism utilizing vacuum to raise the fat layer.

Figure 5:
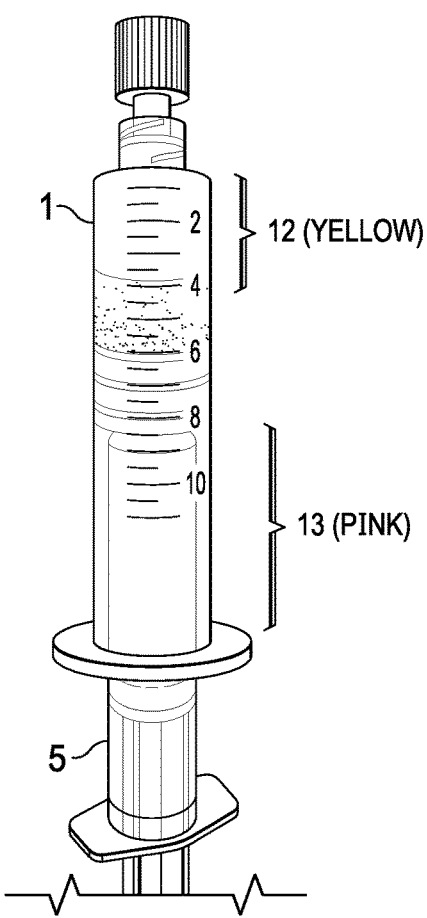
FIG. 5 shows an embodiment of an invention device where a volume of cleaned fat tissue (yellow) is included in the larger outer syringe and a volume of waste in included in the inner syringe (pink).
Figure 9:
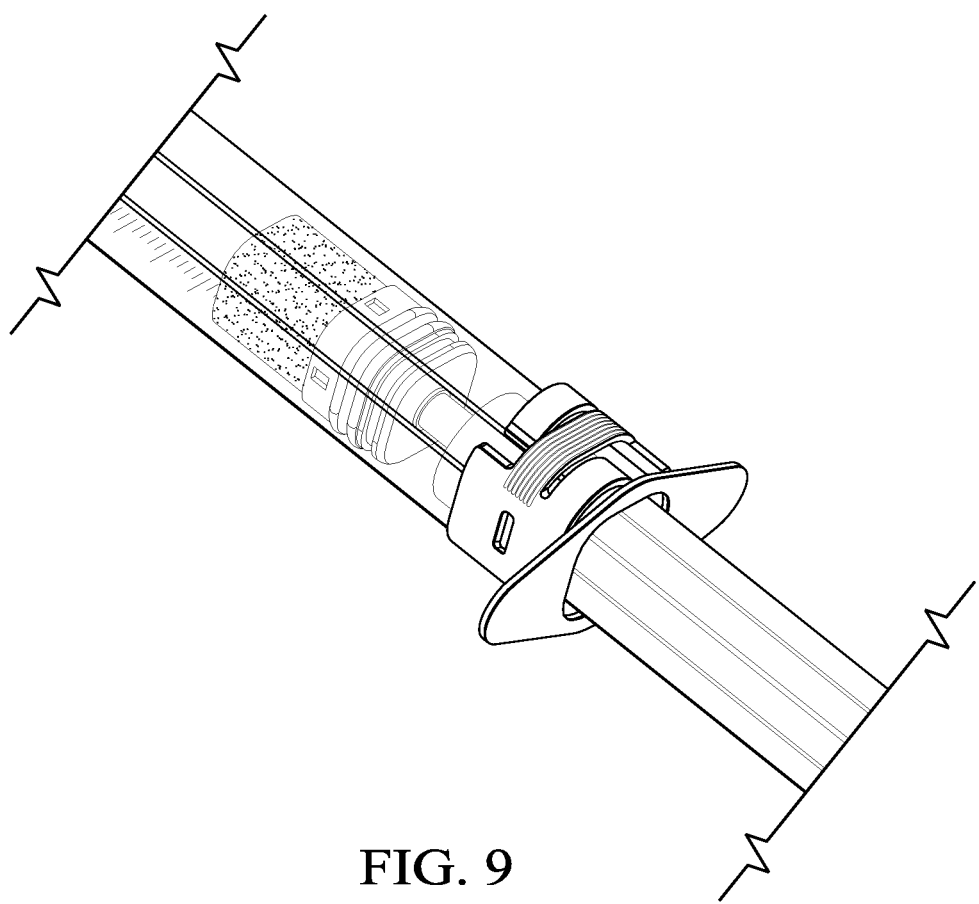
FIG. 9 shows a 60 cc CAD illustration showing square bore syringe and locking button (teal, with ridges).

FIG. 5 describes an assembled invention device embodiment of FIG. 9 in use of tissue harvesting. As shown in FIG. 5, a volume of tissue (12) was collected and cleaned in the outer syringe (1), and the waste (13) was collected in the inner syringe (5).

The description below provides an embodiment procedure of using a syringe of invention (referred to as "PG syringe" or "syringe").

1) Open box that contains the PG syringe, and remove the tray. Peel back the Tyvek to reveal the sterile PG syringe.

2) After a patient is prepared for liposuction, insert a 2 mm cannula (could be included in a kit) into the patient, and pull syringe back until it locks in the vacuum position.
3) Liposuction the patient until syringe is full of lipoaspirate or when a desired volume is harvested.
4) Point syringe up and expel air; cap syringe with included cap. Let sit with tip up for 60 seconds.
5) Drain waste by pulling a vacuum on the waste syringe until tissue is dry.
6) Remove waste syringe, and attach syringe with an amount of saline: inject the saline into tissue.
7) Drain wash by pulling a vacuum on the waste syringe until tissue is dry.
8) Tissue is ready to inject or transfer to desired injection syringe.
9) Dispose of entire PG syringe when finished.

Method of Use

The adipose tissue collected and purified using the invention device can be used in a variety of applications. Such applications (also referred to as "method of use") includes biomedical and cosmetic applications on a subject. Cosmetic applications can be, for example, organ reshaping or augmentation. Biomedical applications can be, for example, tissue grafting, and cell therapy or tissue regenerative therapies.

EXAMPLES

Example 1. Tissue Harvesting Via Micro Needle Liposuction

A closed adipose tissue harvesting and cleaning procedure was successfully carried out using an embodiment invention device of FIG. 4. As shown in FIG. 5, a volume of tissue (12) was collected and cleaned in the outer syringe (1), and the waste (13) was collected in the inner syringe (5). The cleaned adipose tissue 12 is ready for use.

Figure 2:
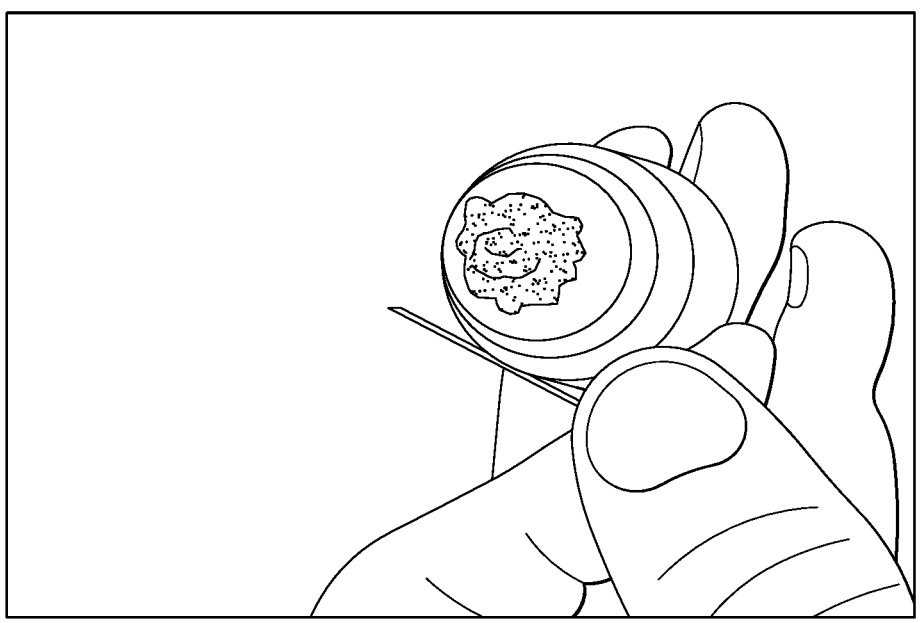

We have successfully combined these requirements into one device that has been used to harvest animal fat. We tested both needle cannulas with animal fat to show that tissue could be collected without clogging of the cannulas. The first test was with the 16 ga needle and the tissue separation device and was able to collect 1-2 grams in just a few minutes. (See FIG. 6) Using animal fat (Pork Bellies) is considered a worst case test for us, in that we cannot really introduce tumescent fluid, and the tissue is at room temperature. But that we were able to collect measurable amount of tissue in a short time was significant. Our initial goal is to be able to collect 5 to IO grams of adipose tissue in less than TO minutes. We tested using a 22 ga. needle modified with 4 side ports. Again, we were able to collect measurable amount of animal tissue in a short period of time. (See FIG. 2) Comparing the two images, you can see that the 22 ga. needle is much smaller, but able to get about the same amount of adipose tissue.

Example 2. Tissue Harvesting Using an Embodiment of Invention Device

FIG. 8 is a photo image of an embodiment of invention device with cleaned tissue (yellow) in the outer syringe and waste product in the inner syringe.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The teachings of the references, including patents and patent related documents, cited herein are incorporated herein in their entirety to the extent not inconsistent with the teachings herein.

We claim:

1. A method of cosmetic or biomedical application on a subject, comprising
    collecting and purifying an adipose tissue from a site of the subject using a device, and
    re-administering the adipose tissue to another site of the subject,
    wherein the device comprising a self-contained syringe device comprising an inner syringe included within an outer syringe that comprises a barrel;
    wherein a filter is attached inside the outer syringe barrel;
    wherein the filter comprises a filter material; and
    wherein lipoaspirated adipose tissue is collected and purified inside the syringes.

2. The method of claim 1, wherein the filter has a mesh pore size between 30 micro meters and 3000 micro meters.

3. The method of claim 1, wherein the inner syringe contained within the outer syringe is adapted to evacuate waste product from lipoaspirated adipose tissue into its barrel the inner syringe is also adapted to contain within its barrel said waste product during reinjection of remaining adipose tissue contained within the filter inside the outer syringe.

4. The method of claim 1, wherein the inner syringe comprises a plunger containing a one-way valve that allows for the passage of waste product from liposuctioned adipose tissue into a barrel of the inner syringe, said one-way valve prevents said waste product from reentering the outer syringe barrel.

5. The method of claim 1, wherein the outer syringe is non-round shaped with a corresponding non-round shaped piston such that the piston is prevented from rotation while the inner syringe is being unscrewed.

6. The method of claim 1, wherein the inner syringe is an inner waste chamber syringe that allows a waste product to evacuate from the lipoaspirated adipose tissue into a separate waste product chamber.

7. The method of claim 1, wherein the inner syringe contains a wash fluid for washing the lipoaspirated adipose tissue, and
    wherein the wash fluid also backflows into the filter to clean the filter.

8. The method of claim 1, wherein the inner syringe attaches to a piston with a luer-activated port, thus the remaining outer syringe and piston forming a self-sealing system when the inner syringe is removed so as to prevent leaking and keep the device a closed system.

9. The method of claim 1, wherein the outer syringe is added grip so as to overcome an issue of grip caused by slipperiness of the adipose tissue.

10. The method of claim 5, wherein the non-round shaped syringe provides extra grip to overcome an issue of grip caused by slipperiness of the adipose tissue.

11. The method of claim 1, wherein the syringe comprises a custom locking mechanism to allow the adipose tissue collection and purification device to be locked in the open position, thereby allowing for holding of a vacuum.

12. The method of claim 1, wherein the device further comprises a needle or a needle hub, wherein the needle or needle hub is attached to the self-contained syringe device.

13. The method of claim 1, wherein the filter material is coated to increase stiffness so as to prevent premature filter collapse.

14. The method of claim 1, wherein the application is organ reshaping or augmentation.

15. The method of claim 1, wherein the application is a tissue grafting, cell therapy or tissue regenerative therapy application.

\* \* \* \* \*